United States Patent [19]

Dowlatshahi

[11] Patent Number: 5,222,953
[45] Date of Patent: Jun. 29, 1993

[54] APPARATUS FOR INTERSTITIAL LASER THERAPY HAVING AN IMPROVED TEMPERATURE SENSOR FOR TISSUE BEING TREATED

[76] Inventor: Kambiz Dowlatshahi, 5490 S. Shore Dr., #7-S, Chicago, Ill. 60615

[21] Appl. No.: 771,306

[22] Filed: Oct. 2, 1991

[51] Int. Cl.$^5$ .............................................. A61B 17/36
[52] U.S. Cl. ...................... 606/15; 128/736; 606/7; 606/42
[58] Field of Search ................ 128/736; 606/2, 7, 9, 606/10, 11, 12, 13, 14, 15, 16, 17, 27, 28, 29, 30, 31, 34, 37, 3

[56] References Cited

U.S. PATENT DOCUMENTS

| | | | |
|---|---|---|---|
| 4,681,122 | 7/1987 | Winters et al. | 128/736 |
| 4,776,334 | 10/1988 | Prionas | 606/42 |
| 4,883,062 | 11/1989 | Nicholson | 128/736 X |
| 4,890,898 | 1/1990 | Bentley et al. | 606/16 X |
| 4,920,978 | 5/1990 | Colvin | 128/736 |
| 4,967,765 | 11/1990 | Turner et al. | 128/736 X |
| 5,061,265 | 10/1991 | Abela et al. | 606/7 |

Primary Examiner—Peter A. Aschenbrenner
Attorney, Agent, or Firm—McCaleb, Lucas & Brugman

[57] ABSTRACT

Improved apparatus for carrying out minimally invasive interstitial laser hyperthermia to induce coagulation necrosis in tissue masses located deeply within the body of a subject. Among examples are malignant tumors in the liver or breast. Low power laser radiation is introduced through an optical fiber extending through a cannula or probe guided into place by medical imaging techniques and inserted directly into the target tissue mass. A thermocouple is secured to the outside of the cannula to sense the temperature of the target tissue irradiated by the laser energy. The thermocouple is located slightly behind the distal end of the cannula and the entire probe assembly is gold plated enabling it to respond primarily to heat transmitted by conduction from the tissue and not by radiation from the laser. In one operating mode described, after the probe is inserted into the tumor, the probe is withdrawn while laser energy is administered at a rate sufficient to maintain the temperature at the thermocouple within a predetermined therapeutic range. In one motorized embodiment, a motor withdraws the cannula at a predetermined speed while the laser is firing, to maintain an effectively high uniform tissue temperature. In another automatic embodiment, the motor speed is controlled in response to the tissue temperature sensed by the thermocouple on the outside of the cannula. This leaves a cylindrical core of necrotic tumor tissue in the wake of the probe as it is drawn through the target tissue.

8 Claims, 2 Drawing Sheets

APPARATUS FOR INTERSTITIAL LASER THERAPY HAVING AN IMPROVED TEMPERATURE SENSOR FOR TISSUE BEING TREATED

BACKGROUND OF THE INVENTION

The present invention relates to contact irradiation treatment of malignant tumors by laser energy, and more particularly to interstitial applications deeply inside the body of a subject.

Non-contact treatment of surface tumors by laser irradiation has become an accepted medical technique for coagulation, necrosis, and palliation of esophageal, bronchial, colorectal and bladder tumors.

Medical researchers are now seriously considering laser techniques for treating deep seated tumors in the liver, pancreas, prostate, and even in the brain. Interstitial techniques of local hyperthermia deep inside the body offers a safe and sometimes the only effective way of treating such tumors. These techniques can be minimally invasive surgically, requiring only a tiny stab incision, dramatically improving patient comfort and chances of survival and reducing convalescence and recovery time in treatment involving the liver for instance.

An apparatus and method for locally generating hyperthermia-induced coagulation necrosis in tissue masses located deeply within the body are described in applicant's co-pending U.S. patent application Ser. No. 07/534,931, filed Jun. 8, 1990 for "APPARATUS AND METHOD FOR INTERSTITIAL LASER THERAPY". As described in that application, low power laser radiation is introduced into the target tissue mass using an optical fiber extending through a cannula which has been inserted directly into the tissue mass. By activating the laser only during withdrawal movement of the cannula and maintaining a small fluid bolus at the fiber tip, effective and reproducible coagulation of tumor tissue is attained without charring or melting of the probe.

One problem in carrying out interstitial hyperthermia is controlling the temperature of the tissue while it is being irradiated. Hyperthermia destroys both tumor tissue and normal tissue. Laser energy delivered by optical fibers inserted directly into tissue provides an excellent form of local hyperthermia for deep seated tumors of clinical importance (in the liver and pancreas, for example). For this to be of maximum effect, treatment parameters required to destroy all the tumor must be known, namely size of the tumor, laser power and exposure time, and number and location of treatment points. There should be minimal damage to adjacent normal tissue, and subsequent healing of all treated areas, so that acceptable function and mechanical structure of the organ is maintained.

While heating alone, at a sufficient elevated temperature and for a sufficient time, is known to destroy tumor tissue, there is considerable experimental and clinical evidence of additional advantages from interaction between Nd:YAG laser radiation and cancer cells. This is believed to be caused by the direct absorption of laser light by the cancer cells. This is reported in *Lasers in Surgery and Medicine* Volume 8, Pages 254–258 (1988) in an article entitled "LASERTHERMIA: A New Computer-Controlled Contact Nd:YAG System for Interstitial Local Hyperthermia".

Thus, there appears to be some cumulative advantage in providing the heat energy needed to kill cancer cells through laser light radiated directly into the cells. Further, the laser of preference is stated to be Nd:YAG in the belief that it penetrates tissue deeper than other types of medical lasers.

Temperature distribution through tissue varies, depending on the color of the organ, the rate of blood flow through the organ, and the level of energy applied. In the "LASERTHERMIA . . . " article cited above, a thermogram comparison made in heat conductivity studies on spleen tissue showed the tissue temperature ranged from 50° C. at the heat source to 43° C. six millimeters away, with laser energy input of approximately 5 watts.

Recognizing the importance of keeping the tissue temperature high enough to destroy cancer cells, some prior medical researchers have implanted thermocouples in the tissue to be treated. In applicant's copending application Ser. No. 07/534,931, separate, parallel needles are glued together, 3 mm. apart. One carries an optical fiber and the other carries a temperature-sensing thermocouple. While this is useful as a research tool, it would have serious disadvantages in the real world of practical medical treatment.

In the example mentioned above where the implanted thermocouples were stationary, they could be used only with stationary laser probes because movement of the probes would make the temperature readings meaningless.

Even in the case of the double needle embodiment disclosed in applicant's copending application, it would be very difficult to precisely control the spacing between the thermocouple and the laser tip, especially with long probes. Further, it would require multiple stab incisions or a relatively large incision.

SUMMARY OF THE INVENTION

Accordingly, it is an object of the present invention to provide an apparatus and method for treatment of tumor tissues located inside organs within the body by laser-induced hyperthermia and coagulative necrosis, with improved precision control of the tissue temperature.

Another object of this invention is to provide an apparatus and method for accurately monitoring the temperature of the tumor tissue being treated by securing a temperature sensing element directly to a laser energy transmitting probe which is insertable directly in the tumor tissue.

Another object of this invention is to provide an apparatus and method for simultaneously monitoring the temperature of tumor tissue within which a laser energy transmitting probe is inserted while moving the probe throughout the tissue at a speed which will heat successive regions of the tissue uniformly to a predetermined therapeutic temperature range during movement of the probe.

Another object of the invention is to provide an apparatus and method for moving a laser energy transmitting probe through a tumor tissue while monitoring the temperature of the tissue at the probe and regulating the speed of movement of the probe to maintain the temperature at the probe within a predetermined therapeutic temperature range.

Another object of the invention is to provide an apparatus and method for moving a laser energy transmitting probe through a tumor tissue while monitoring the temperature of the tissue at the probe and regulating the energy input to the probe to maintain the temperature of the tissue at the probe within a predetermined therapeutic temperature range.

Another object of the invention is to provide apparatus for interstitial laser therapy comprising a thin cannula, an optical fiber extending through a lumen in the cannula to conduct laser energy to a tissue mass in which the distal end portion of the cannula is inserted, and a temperature sensing element secured to the surface of the cannula at the distal end portion and movable therewith.

Another object of the invention is to locate the temperature sensing element rearwardly of the distal tip of the cannula a sufficient distance to render the temperature sensing element sensitive primarily to the heat of the tissue mass in which the distal end portion of the cannula is inserted.

Another object is to provide, on the temperature sensing element and adjacent portion of the cannula, a highly reflective coating having reflectivity in the order of gold plating, enabling the temperature sensing element to respond primarily to heat conducted from tissue in which the distal end portion of the cannula is inserted, and not from heat reflected directly or indirectly from the tip of the optical fiber.

Another object is to provide the temperature sensing element in the form of a miniature thermocouple or thermistor at the forward end of a miniature tube which is smoothly soldered or otherwise inconspicuously secured along the outside of the cannula.

BRIEF DESCRIPTION OF THE DRAWINGS

Other objects and advantages will be apparent from the following drawings in which.

Like parts are designated by like reference characters throughout the figures of the drawing.

DESCRIPTION OF THE PREFERRED EMBODIMENT

Figure 1:
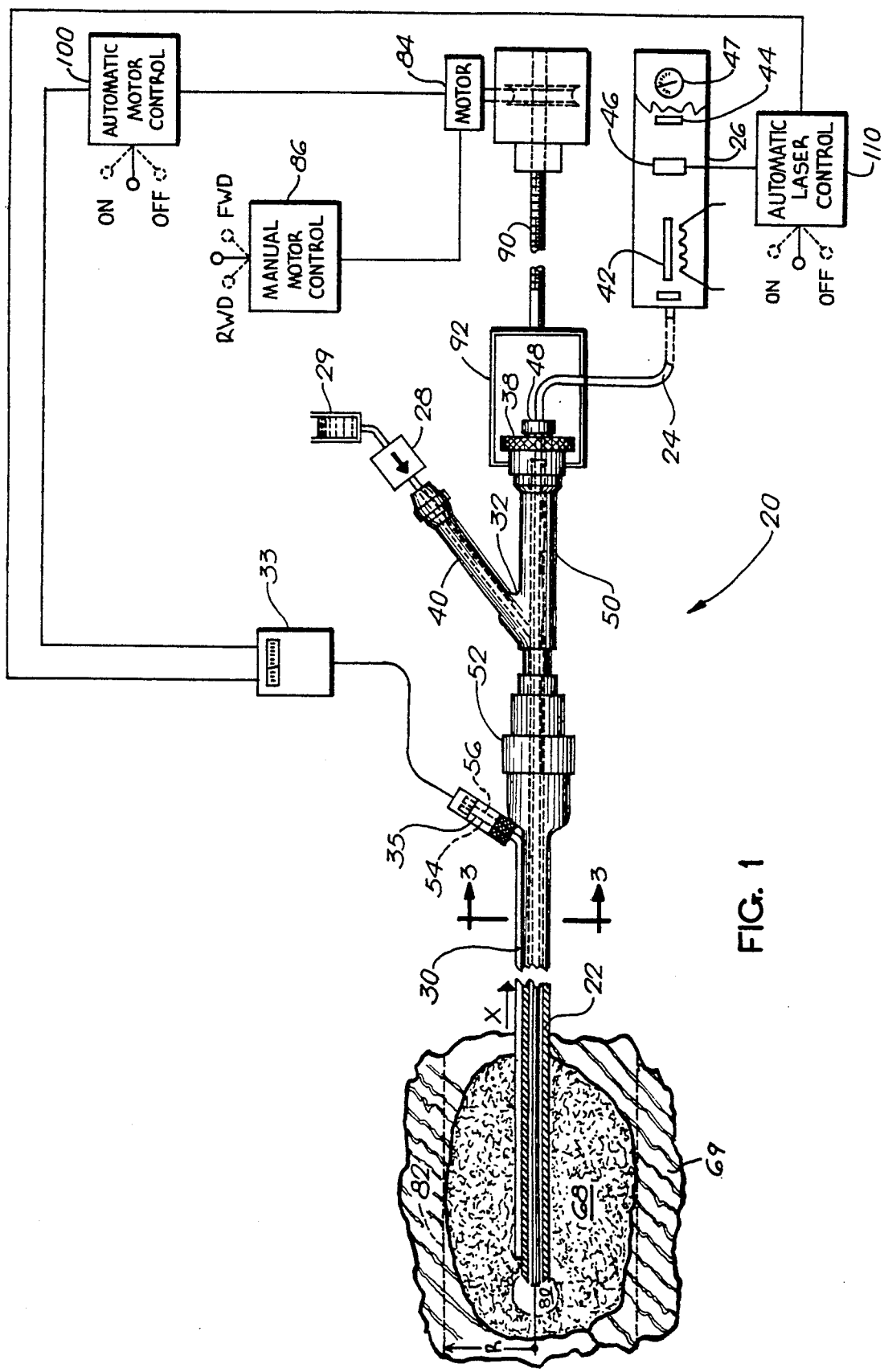
FIG. 1 shows a schematic representation of a side view of the apparatus of the present invention illustrating the cannula, the optical fiber, the temperature sensing element secured to the outside of the cannula, a commercially available Y-connector supporting the cannula, a longitudinal positioning stop for the optical fiber, a tissue mass into which the cannula is inserted, and components for operating in a manual mode or in optional automatic modes.

Referring now to the embodiment shown in the drawings, the apparatus is generally designated 20. This comprises a thin needle cannula or probe 22, an optical fiber 24, a laser 26, a pump 28, a source of physiologically acceptable fluid 29, temperature sensing means 30, and a Y-connector 32.

The needle cannula 22 may be an extra thin 19-gauge stainless steel needle (1.1 millimeter outside diameter, and less than 100 microns wall thickness). Alternatively, it may be made of an anatomically acceptable plastic or elastomeric material having suitable rigidity. The internal diameter of the lumen 34 in the cannula is sufficiently large to allow for easy location of the optical fiber 24 as well as to permit para-axial flow of a cooling fluid such as normal saline from pump 28 and a syringe or other source 29. The cannula may be any suitable length, e.g., 10–15 cm, to reach tissue masses to be treated which are distant from the skin surface.

The optical fiber for use with the cannula may be a 600 micron diameter quartz optical fiber having a divergence angle of 8° and it will be stripped of its terminal plastic coating sufficiently to allow the stripped portion to be inserted through the lumen 34. Smaller diameter optical fibers can be employed for the purposes of the present invention, allowing smaller cannulae to be used, thereby significantly diminishing the adverse effects of insertion of the apparatus into deeply-lying tumors in otherwise healthy tissue.

The laser 26 is preferably a Nd:YAG laser generating radiation coupled into optical fiber 24 which passes through the Y-connector 32.

Figure 3:
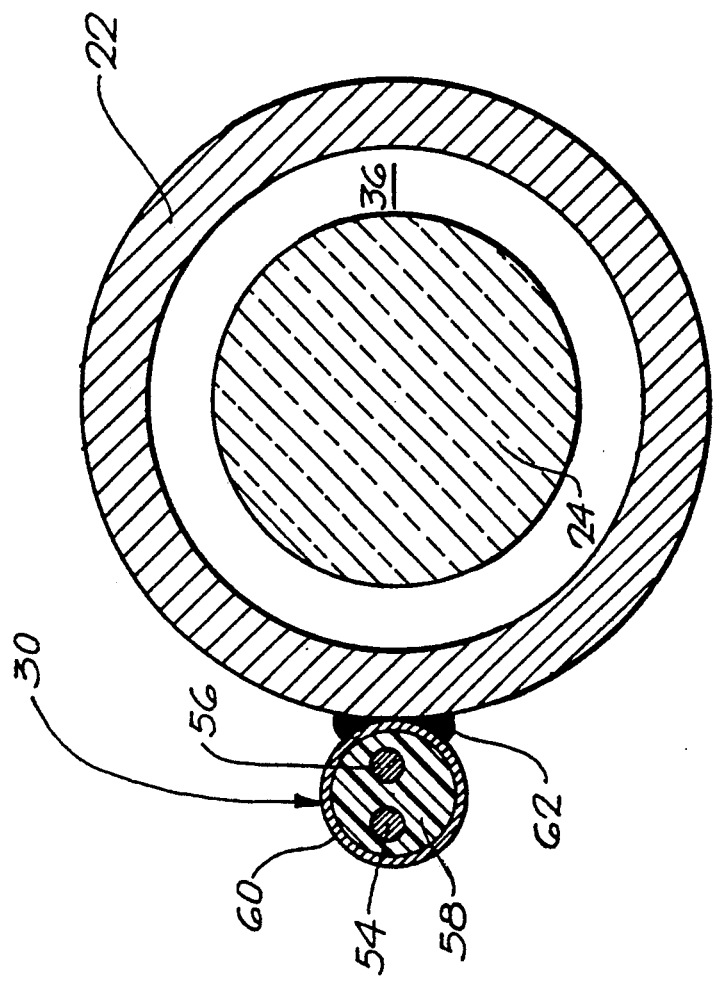
FIG. 3 is a greatly enlarged cross sectional view of FIG. 1 taken along line 3—3.

The fluid pump 28 may be a micro pump supplying, for example, normal saline fluid through the annular space 36 (FIG. 3) between the cannula 22 and optical fiber 24. As described in applicant's co-pending application Ser. No. 07/534,931, this normal saline acts as a cooling fluid and also provides a heat transfer and dispersing medium for the laser energy from the optical fiber tip to the tissue mass being treated, thereby avoiding direct heat concentration and possible charring of tissue at the distal tip end of the optical fiber. Prior to insertion, the position of the optical fiber in the cannula is adjusted so that the distal tip is approximately flush with the tip of the cannula 22 before tightening the proximal screw 38 of the Y connector 32. If the distal tip of the fiber is located significantly inside of the cannula, excessive heating of the cannula results, while if the tip is located significantly forwardly of the cannula tip, the saline fluid is ineffective. In practice the fiber tip may extend up to about a millimeter beyond the cannula tip. Fluid pump 28 is connected to arm 40 of Y-connector 32.

Laser 26 has a laser rod 42, a resonant mirror 44, and a shutter 46 between them. The emission of a laser beam from the source 26 is controlled by the shutter 46. Laser energy output in watts may be indicated by dial 47 on the outer casing. The laser 26 directs laser energy into the optical fiber 24. A stop collar 48 is secured on the optical fiber to fix the horizontal position of the distal tip approximately flush with the tip of the cannula 22. A second, straight arm 50 of Y-connector 32 guides the optical fiber into the coupling 52 at the proximal end of the cannula.

Figure 4:
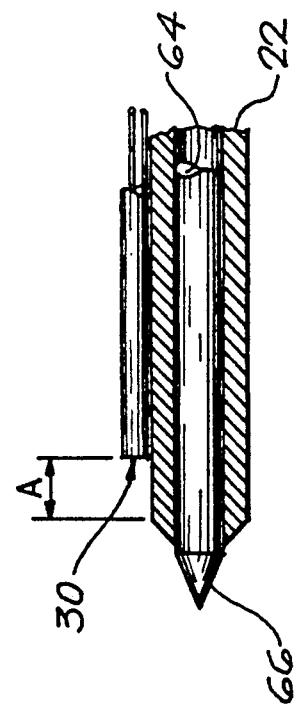
FIG. 4 is a fragmentary enlarged view of the distal end portion of the cannula with a pointed stylet inserted therein to facilitate insertion into a tissue mass to be treated.

The temperature sensing means 30 may for example be a 0.010 inch micro thermocouple (Omega, Conn.). This is soldered smoothly to the outside of the needle cannula with its tip located one millimeter proximal to the tip of the cannula. Referring to FIG. 4, the dimension A is one millimeter. As shown in the cross section of FIG. 3, a pair of conductors 54, 56 extend rearwardly through insulation 58 within a mini tube or casing 60 connected as by solder 62 along the outside of the cannula 22.

In using the apparatus to ablate a tumor, the size and dimensions of the tumor will first be determined. Correct measurement of the tumor is important in using the apparatus and method of this invention. The laser energy and exposure time for a particular tumor will be determined from data tables prepared in advance from prior hyperthermia tests with similar apparatus on various size tumors in animal and human subjects. With presently available medical imaging technology such as computerized tomography and ultrasound, it is possible to measure tumor volumes both pre-, intra- and post-operatively. Information derived from this type of investigation makes it possible to calculate the total amount of energy in joules (watt-seconds) required for an average 2-3 centimeter diameter tumor occurring in the breast and liver. Previous investigators have reported the penetration of Neodymium:Yttrium-Aluminum-Garnet (Nd:YAG) laser light and "cell kill" to range between 3-8 millimeters for both contact and interstitial applications ("Nd:YAG Laser-Induced Hyperthermia in a Mouse Tumor Model"-*Lasers in Surgery and Medicine,* 1988; 8:510-514). Factors such as tumor type, pigmentation of the tissue mass, vascularity, and type of laser energy will influence the ablative outcome.

Figure 2:
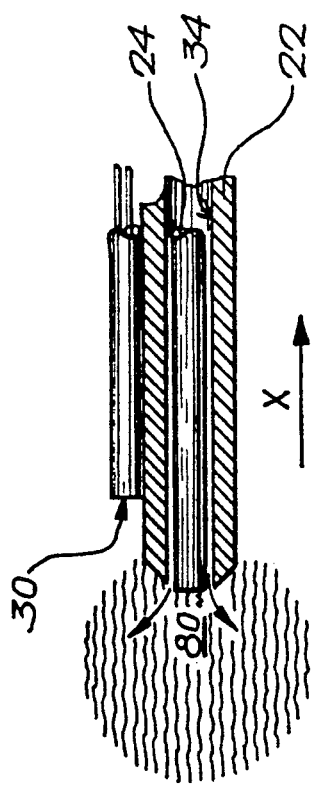
FIG. 2 is a fragmentary enlarged view of FIG. 1.

In operation, a stylet 64 will be assembled in the cannula with the point 66 extending from the distal end as shown in FIG. 4. The length of the cannula and stylet will be determined by the depth of the tumor within the body. Under general anesthesia, the cannula and stylet will be inserted through a small stab incision in the skin and guided precisely through normal tissue 69 into the tumor mass 68 using known medical imaging technology. The cannula needle with the stylet 64 is inserted along the longitudinal axis of the tumor mass 68 to the far end as shown in FIG. 1. The stylet will then be withdrawn and replaced by the optical fiber 24 with the tip flush with the distal end of the cannula as determined by the stop collar 48. This is shown in FIGS. 1 and 2. At this time, the mini-pump 28 is started and draws normal saline from source 29 and flows it into the annular space 36 between the optical fiber 24 and cannula 22. This causes a continuous flow of saline, for example in the order of one cubic centimeter per minute. The fluid exiting the distal end of the cannula produces a bolus 80 of liquid which prevents overheating damage to the fiber tip, and acts as a lens transmitting and dispersing laser light energy transversely of the optical fiber tip. As reported in the article entitled "LASERTHERMIA . . . " cited above, where the temperature in the immediate vicinity of an interstitial probe was held at 50° C., the temperature 6 to 7 millimeters away (at the radius R, FIG. 1) was maintained at 42°-43° C. which resulted in tumor necrosis of 70%-80% within 7 days.

Applying the above heat distribution findings in the practice of this invention to FIG. 1, laser 26 is fired until the temperature sensed by the thermocouple 30 is 50°-51° C. This means that the temperature at the radius R is 42°-45° C. Then, by withdrawing the cannula, in the direction of the arrow X, at a speed sufficient to keep the temperature at the thermocouple between 50°-51° C., the tumor mass 68 will be effectively locally destroyed at least out to the radius R with minimal loss of normal tissue. For larger tumors, multiple passes may be made with the cannula, or in some cases the laser energy level may be increased. However, excessively high levels of energy should be avoided to avoid liquifaction. The thermocouple 30 and mini-tube 60 will preferably be gold plated to prevent transmission of heat from the bolus 80 by direct or indirect reflection; thereby rendering the thermocouple 30 primarily responsive to heat received from the tumor mass by conduction. This greatly improves the accuracy of temperature measurement at the thermocouple tip 30.

In practicing the invention, the following three modes of operation are available to maintain a predetermined therapeutic temperature in the tumor tissue mass while withdrawing the cannula: (1) a manual mode; (2) a first automatic mode in which speed of movement of the cannula varies automatically in response to tissue temperature; and (3) a second automatic mode in which laser input energy varies automatically in response to tissue temperature.

Referring first to the manual mode, the cannula 22 is fitted with a pointed stylus 64 as shown in FIG. 4 and introduced through a small stab incision and guided by conventional medical imaging technology and is inserted preferably along the longitudinal axis to the far end of the mass. The stylet will be removed and replaced by the optical fiber as shown in FIGS. 1 and 2. The size of the tumor will already have been determined by previous medical imaging and the laser energy and exposure time for the particular tumor will have been determined from data tables prepared in advance as stated above.

For example, if the tumor has a 6 mm radius and the data tables show that a 5-watt energy input by the laser 26 will produce a temperature of 50°-51° C. on the outer surface of the distal end of the cannula sensed by the thermocouple 30, and this in turn will produce a temperature of 42°-45° C. at the radius R=6 mm, this is sufficient to destroy a circular area of similar tumor tissue having the same 6 mm radius. At the outset, the surgeon or technician allows a few drops of saline to flow through the annular space 36 to displace any air, tissue debris or blood clots entrained therein. The saline pump 28 will be adjusted at a desired rate, typically, one cubic centimeter per minute, enough to establish a fluid pool or bolus 80 in front of the distal tip of optical fiber 24 as described in applicant's copending application Ser. No. 07/534,931 to which reference may be made for details. Next, the laser is activated and set for an output of 5 watts. When the temperature gauge 33 indicates that the temperature at thermocouple 30 is in the predetermined range of 50°-51° C., the motor 84 is activated in a rearward direction. Speed is regulated by the manual motor control 86 to keep the tissue temperature at the thermocouple in that predetermined range so the temperature at the radius R (FIG. 1) reaches 42°-45° C. progressively along the axis of the cannula to thereby coagulate a cylindrical volume 82 of tissue as the cannula is withdrawn. This movement is observed by medical imaging and terminated when the tip of the cannula reaches the proximal end of the tissue mass.

In practicing the invention by the first mentioned automatic mode, after the cannula is inserted in the tumor mass 68, and the bolus 80 is established by saline pump 28, the output energy of laser 26 may be set at 5 watts, for example. An automatic motor control unit 100 is schematically shown connected between the temperature gauge 33 and motor 84. Control unit 100 will be set to activate motor 84 in a direction to reverse-rotate screw 90 and thereby withdraw the cannula 22 when the temperature sensed by gauge 33 reaches 51° C. or more, and to stop when the temperature is at 50° C. or less. Thus control 100 and motor 84 automatically regulate the withdrawal rate to maintain the tissue temperature within the predetermined therapeutic range which in this example is assumed to be 50°-51° C. at the surface of the cannula and corresponds to 42°-45° C. at radius R.

In practicing the invention by the second mentioned automatic mode, after the cannula is inserted in the tumor mass 68, and the bolus 80 is established by saline pump 28, the motor 84 will be turned on and set at a desired reverse speed by control 86. Automatic laser control 110 is connected between temperature gauge 33 and energy output control shutter 46 of laser 26. Control 110 will be set to turn the laser on when the temperature sensed by thermocouple 30 is 50° C. or less and to turn the laser off when the temperature sensed by the thermocouple is 51° C. or above. Thus, control 100 and laser 26 automatically regulate the energy input through the optical fiber to maintain the tissue temperature within the predetermined therapeutic temperature range.

In order that those skilled in this art may better understand the invention, the following detailed description taken from clinical tests is presented in detail.

EXAMPLE

Laser Probe

A prototype probe as shown in FIG. 1 was employed in this investigation. It consisted of a 10 cm long 19-gauge needle cannula 22 containing a stylet 64 which facilitated the initial insertion and was subsequently replaced by the laser optical fiber 24. A 0.010 inch micro thermocouple 30 (Omega, Conn.) was soldered employing pure tin to the outside of the needle cannula with its tip located exactly one millimeter proximal to the tip of the cannula. This complex was gold plated to reflect direct laser light. The plug 35 on the proximal end of thermocouple conductors 54, 56 was connected to the temperature gauge 33 for continuous temperature display. This plug was secured to the hub of the needle cannula by epoxy. A 600 micron bare tip quartz fiber was stripped of its terminal 10.5 cm cladding and passed through the straight arm 50 of the Y-connector 32 (Advanced Cardiovascular System, Calif.) Its position was fixed by tightening the screw 38 around the laser fiber cladding, so that the bare tip on the distal end would protrude less than one millimeter from the end of the cannula. In other words, the tip of the optical fiber was very slightly outwardly located from a flush position with respect to the distal end of the cannula.

Tumor Model

Virgin, female Sprague-Dawley rats at 50 days of age and approximately 200 grams were injected with N-methyl-N-nitrosourea at a dose of 40 milligrams per kilogram body weight to induce mammary carcinomas. After an interval of approximately 2 months, each animal was palpated once a week to assess tumor growth. Tumors measuring 2 centimeters in diameter or larger were selected for this experiment.

Methods

The animals were anesthetized with an intramuscular injection of ketamine at a dose of 44 milligrams per kilogram body weight. The hair around each tumor and surrounding area was shaved and the tumor dimensions were measured with a caliper. The tumor was immobilized without occluding its blood supply with a non-crushing clamp. The cannula 22 with a stylet 64 in the cannula was inserted along the longitudinal axis of the tumor 68 and was advanced until its tip could be palpated subcutaneously on the opposite pole of the tumor. The stylet 66 was removed and the laser fiber 24, already fixed inside the "Y" shaped connector 32 to a predetermined length, was inserted in the needle cannula 22, and the tightening screw 38 was tightened on the cannula. Arm 40 of the Y-connector 32 was attached to a syringe 39 filled with normal saline and placed in a Harvard pump 28 (Harvard Biosciences, Me.) This allowed a continuous flow of saline (1 cc/min) to prevent damage to the fiber tip during irradiation. This is described in "Lasers in Surgery and Medicine", 10:322–327 (1990), in an article by Kambiz Dowlatshahi, Julie D. Bangert, Michael F. Haklin, Charles K. Rhodes, Ronald S. Weinstein, and Steven G. Economou, entitled "PROTECTION OF FIBER FUNCTION BY PARA-AXIAL FLUID FLOW IN INTERSTITIAL LASER THERAPY OF MALIGNANT TUMOR". The "thermo-laser probe" was attached to a Sears Lathe and set to move out of the tumor.

Five animals, with one tumor each, were allocated to each of five levels of laser irradiation: 500, 750, 1000, 1500 and 2000 joules (J), respectively. Tumors measuring 2 cm in diameter were chosen for up to 1000 J irradiation and 3 cm tumors for the 1000–2000 J experiments. There were two control groups with 5 tumors in each. In the first control group, the laser probe was inserted and saline administered (1 cc/min) as the probe was withdrawn but no laser energy was given. In the second control group, the tumors were excised and sectioned without probe insertion to assess the degree of spontaneous necrosis. At the outset, approximately 0.5 cc of saline was allowed to flow before activating the laser at a power setting of 5 watts. Once the temperature reached 42° C., the laser probe was slowly withdrawn at a speed to ensure that the temperature of the tumor remained between 42°–45° C. The fiber transmission was tested at the beginning and at the end of each experiment using a power meter (Trimedyne, Calif.).

48 hours later, again under general anesthesia, the laser treated tumors and tumors from the first control group were excised and fixed in 10% buffered formalin. The tumors which were liquified or partially ulcerated (total of 17), hence non-evaluable with respect to volume determination, were excluded and replaced. Intact tumors were serially sectioned in 3 mm slices, and representative sections were taken from each block and stained with hematoxylin and eosin. Each section was individually examined under microscope employing a Nikkon Labophot with a 1X objective (Fryer, Ill.). A JVC video camera in conjunction with a Macintosh II Image Studio program was employed to measure the surface area of the necrotic tissue. The coagulated volume of each block was determined by multiplying the mean surface area of necrosis by the thickness of the block. The sum of the individual necrotic volumes of all blocks was the total volume of coagulated tissue caused by interstitial laserthermia in that tumor.

Results

The rat mammary tumors (adenocarcinomas) treated with Nd:YAG laser hyperthermia in this study uniformly exhibited coagulation necrosis at 48 hours. Centrally, the cytoplasmic membrane of the cells was disrupted and nuclear pyknosis was marked. Peripherally, although cell kill was still evident, the overall outline of the lobule was preserved.

The volume of necrosis incrementally increased in tumors receiving greater quantities of laser energy as shown in Table 1.

TABLE 1

| TOTAL ENERGY (joules) | VOLUME OF NECROSIS (cc) MEAN (RANGE) |
| --- | --- |
| 0 | 0.2 (0.1–0.3) |
| 500 | 0.8 (0.5–1.1) |
| 750 | 1.2 (0.6–1.9) |
| 1000 | 1.4 (1.3–1–6) |
| 1500 | 2.4 (1.6–3.6) |
| 2000 | 4.0 (2.1–5.2) |

Isolated islands of necrosis, "skip lesions", were noted outside the main ablated area, in tumors irradiated with 500–750 joules, but were not included in the histologic measurement of their necrotic volumes. A linear relationship was observed between laser energy and the volume of necrosis. Since the necrotic volumes could not be adequately ascertained in the liquified tumors, these were replaced. The following Table 2 illustrates that 19 of the 44 tumors used in this study liquified and that the incidence of liquefaction increased with greater levels of irradiation.

TABLE 2

| JOULES | LIQUIFIED TUMORS NUMBER OF TUMORS (% OF TOTAL*) |
| --- | --- |
| 500 | 1 (16%) |
| 750 | 3 (36%) |
| 1000 | 4 (44%) |
| 1500 | 5 (50%) |
| 2000 | 6 (56%) |

*PERCENTAGE OF THE TOTAL NUMBER OF TUMORS TREATED IN THAT ENERGY CATEGORY

The results from these experiments indicate that continuous wave Nd:YAG laser at 5 watts delivered interstitially through a mobile probe can ablate 1 cc of rat mammary tumor in 2 minutes. If the tumor temperature is maintained within 42°–45° C., the rate of fiber transmission loss is less than 1% after 1000 J of irradiation.

Discussion

The tumor model chosen for this study was very cellular and moderately vascular. The superficial location of the tumors along the mammary ridge enabled the insertion of the laser probe into the central axis of the tumor with relative ease and without the need for sonographic guidance. Forty three percent of the treated tumors liquified of which 79% received greater than 1000 J of energy. Even though tumors of larger size were utilized for the higher energy levels, the incidence of liquefication still increased. This may be a reflection of the limitation of this tumor model to absorb high energy or simply the tumor outgrowing its blood supply and to be susceptible to excessive necrosis.

The para-axial fluid flow allowed the coagulation of a 2 cm tumor within 10 min using continuous wave Nd:YAG laser set at 5 watts with minimal damage to the fiber tip. Initially a power setting of 10 watts was employed to accelerate the process and shorten the operation time but this higher power setting resulted in more damage to the laser fiber tip, necessitating replacement.

SUMMARY OF THE EXPERIMENTAL TESTS

The extent of coagulative necrosis caused by interstitial laser hyperthermia was measured for different quantities of laser energy in a rat mammary tumor model. Continuous wave Nd:YAG laser at a power level of 5 watts was focused onto a 600 micron diameter bare tip quartz fiber and placed inside a 19-gauge needle which allowed the para-axial flow of normal saline at 1 cc/min. A microthermocouple soldered to the outside of the probe continuously provided the interstitial temperature. After the probe was inserted into the tumor, it was withdrawn as laser energy was administered at a rate sufficient to maintain the temperature within 42°–45° C. Tumors were excised after 48 hours, fixed in formalin, cut in 3 mm slices and the coagulated surfaces measured microscopically. Laser fiber transmission loss was 1% per 1000 joules of laser energy and the average time required to coagulate 1 cc of tumor was 2 minutes. The mean volume of tumor necrosis of five experiments at each level of laser irradiation was:

| Laser energy (joules) | 500 | 750 | 1000 | 1500 | 2000 |
| --- | --- | --- | --- | --- | --- |
| Tumor necrosis (cc) | 0.8 | 1.2 | 1.4 | 2.4 | 4.0 |

It is concluded that the described technique is an efficient method of tumor coagulation by interstitial laser hyperthermia and proportionally larger volumes of necrosis are created with greater amounts of laser energy.

While the above description illustrates specific apparatus and methods for practicing this invention, the invention is not limited thereto and includes all embodiments which would be apparent to those skilled in the art.

The embodiments of the invention in which an exclusive property or privilege is claimed are defined as follows:

1. Apparatus for interstitial laser therapy comprising in combination:

a thin cannula for insertion in a tissue mass, said cannula having a lumen extending axially between proximal and distal end portions and a distally facing central axial opening at the distal end communicating with the lumen, said lumen being adapted to receive an optical fiber for transmitting laser energy into a tissue mass in which the distal end portion of the cannula is inserted;

a temperature sensing means secured to the outside of the distal end portion of the cannula and movable therewith to sense temperature of a tissue mass in which the distal end portion of the cannula is inserted; and said temperature sensing means is proximally spaced from the outside distal end of the cannula to be out of a direct line of view with said central axial opening.

2. Apparatus for interstitial laser therapy according to claim 1 in which an optical fiber is disposed in said lumen and the distal end of the optical fiber is substantially flush with the distal end of the cannula and effective when laser energy is applied to the proximal end of the optical fiber to emit laser energy distally and axially from the distal end of the optical fiber.

3. Apparatus for interstitial laser therapy comprising in combination:

a thin cannula for insertion in a tissue mass, said cannula having a lumen extending between proximal and distal end portions and being adapted to receive an optical fiber for transmitting laser energy into a tissue mass in which the distal end portion of the cannula is inserted;

a temperature sensing means secured to the outside of the distal end portion of the cannula and movable therewith to sense temperature of a tissue mass in which the distal end portion of the cannula is inserted; and said temperature sensing means and at least the immediately adjacent surface of the cannula having a highly reflective surface having reflectivity in the order of magnitude of gold plating;

whereby the temperature sensing means is sensitive primarily to heat received by conduction and not by reflection from tissue in which the distal end portion of the cannula is inserted.

4. In apparatus for interstitial laser therapy including a thin cannula having a lumen for insertion in a tissue mass, said cannula having a lumen extending between proximal and distal end portions and an optical fiber in said lumen for transmitting laser energy into a tissue mass in which the distal end portion of the cannula is inserted, the improvement comprising:

a temperature sensing means secured to the outside of the distal end portion of the cannula and movable therewith to sense temperature of a tissue mass in which the distal end portion of the cannula is inserted; and said temperature sensing means and at least the immediately adjacent surface of the cannula having a highly reflective surface having reflectivity in the order of magnitude of gold plating;

whereby the temperature sensing means is sensitive primarily to heat received by conduction and not by reflection from tissue in which the distal end of the cannula is inserted.

5. In apparatus for interstitial laser therapy including a thin cannula having a lumen for insertion in a tissue mass, said cannula having a lumen extending between proximal and distal end portions and an optical fiber in said lumen for transmitting laser energy into a tissue mass in which the distal end portion of the cannula is inserted, the improvement comprising:

a temperature sensing means secured to the outside of the distal end portion of the cannula and movable therewith to sense temperature of a tissue mass in which the distal end portion of the cannula is inserted; and motor-driven means connected to the cannula for withdrawing the cannula at predetermined speed from tissue in which the distal end portion of the cannula is inserted.

6. In apparatus for interstitial laser therapy, the improvement of claim 5 including temperature indicating means connected to said temperature sensing means to read a temperature sensed thereby, and automatic means for controlling the motor-driven means in response to the temperature indicating means to regulate speed of withdrawal of the cannula for maintaining temperature at the temperature sensing element within a predetermined therapeutic temperature range.

7. In apparatus for interstitial laser therapy, the improvement of claim 5 including temperature indicating means connected to said temperature sensing means to read a temperature sensed thereby laser generating means;

means for transmitting laser energy from said laser generating means into said optical fiber; and automatic means for regulating the laser energy transmitted to the optical fiber in response to the temperature indicating means to thereby maintain the temperature of tissue sensed by said sensing means within a predetermined therapeutic temperature range.

8. Apparatus for interstitial laser therapy comprising in combination:

a thin cannula for insertion in a tissue mass, said cannula having a lumen extending between proximal and distal end portions, said cannula having a distal end opening at the distal end of the lumen which is adapted to receive an optical fiber for transmitting laser energy into a tissue mass in which the distal end portion of the cannula is inserted;

a temperature sensing means secured to the outside of the distal end portion of the cannula and movable therewith, said temperature sensing means facing distally toward tissue beyond said distal end portion to sense temperature of such tissue heated by a laser beam transmitted through said distal end opening; and said temperature sensing means is spaced sufficiently from the outside distal end of the cannula that it is shaded from direct view of said opening and therefore is essentially non-responsive to laser energy emitted through said distal end opening;

whereby said temperature sensing means is primarily responsive to temperature of tissue beyond said distal end portion.

* * * * *